(12) United States Patent
Yoshii et al.

(10) Patent No.: US 7,981,839 B2
(45) Date of Patent: Jul. 19, 2011

(54) HERBICIDAL SUSPENSION

(75) Inventors: Hiroshi Yoshii, Kusatsu (JP); Yoshiaki Ishihara, Kusatsu (JP); Ryu Yamada, Kusatsu (JP); Tatsuhiko Tsuruta, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 679 days.

(21) Appl. No.: 11/908,521

(22) PCT Filed: Feb. 23, 2006

(86) PCT No.: PCT/JP2006/303918
§ 371 (c)(1),
(2), (4) Date: Sep. 13, 2007

(87) PCT Pub. No.: WO2006/098156
PCT Pub. Date: Sep. 21, 2006

(65) Prior Publication Data
US 2009/0029862 A1    Jan. 29, 2009

(30) Foreign Application Priority Data

Mar. 14, 2005 (JP) ................................. 2005-072034
Dec. 15, 2005 (JP) ................................. 2005-361424

(51) Int. Cl.
*A01N 47/28* (2006.01)
*A01N 47/34* (2006.01)
*A01N 41/06* (2006.01)
*A01N 25/02* (2006.01)

(52) U.S. Cl. ........ 504/215; 504/211; 504/329; 504/362; 504/364; 514/601

(58) Field of Classification Search ............... 504/211, 504/215, 362, 364; 514/601
See application file for complete search history.

(56) References Cited

U.S. PATENT DOCUMENTS

| 4,824,475 | A | | 4/1989 | Markley et al. | |
|---|---|---|---|---|---|
| 5,208,212 | A | * | 5/1993 | Poss et al. ..................... | 504/139 |
| 5,889,088 | A | * | 3/1999 | Kisuno et al. ................. | 523/205 |
| 6,479,432 | B1 | * | 11/2002 | Sixl ................ | 504/103 |
| 2002/0045549 | A1 | * | 4/2002 | Kruger et al. ................. | 504/211 |
| 2006/0154824 | A1 | | 7/2006 | Yoshii et al. | |

FOREIGN PATENT DOCUMENTS

| AP | 112 | 3/1990 |
|---|---|---|
| CN | 1031081 A | 2/1989 |
| DE | 199 51 427 | 5/2001 |
| EP | 0 341 011 | 11/1989 |
| EP | 0 475 392 | 3/1992 |
| EP | 0 598 515 | 5/1994 |
| WO | 89 01289 | 2/1989 |
| WO | 2005 009132 | 2/2005 |

OTHER PUBLICATIONS

U.S. Appl. No. 12/280,567, filed Aug. 25, 2008, Yoshii et al.

* cited by examiner

*Primary Examiner* — John Pak
*Assistant Examiner* — Andriae M Holt
(74) *Attorney, Agent, or Firm* — Oblon, Spivak, McClelland, Maier & Neustadt, L.L.P.

(57) ABSTRACT

A herbicidal suspension comprising (1) a sulfonylurea compound or its salt as a herbicidal component, (2) at least one surfactant selected from the group consisting of an alkoxylated sorbitol fatty acid ester and an alkoxylated sorbitan fatty acid ester, and (3) a water-immiscible diluent. A method for controlling undesired plants or inhibiting their growth, which comprises applying a herbicidally effective amount of the herbicidal suspension to the undesired plants or to a place where they grow.

16 Claims, No Drawings

HERBICIDAL SUSPENSION

TECHNICAL FIELD

The present invention relates to a herbicidal suspension containing a sulfonylurea compound or its salt as a herbicidally active ingredient, and having a stable herbicidal effect, safety for crops and practically satisfactory effects.

BACKGROUND ART

In recent years, various studies have been conducted to obtain agricultural chemicals which stably exhibit a favorable herbicidal effect, which have no harmful effect over crops and which can be used safely. Further, there is a tendency to employ various additives for agricultural chemicals which can reduce harmful effects of the agricultural chemicals over human and environment as far as possible.

Under these circumstances, it has been desired to quickly develop alternatives to conventional agricultural chemicals having the above-described problems, and to supply to the market agricultural chemicals which are human- and environmentally-friendly and which are also practical.

EP 0598515 discloses an activity-enhanced herbicidal composition comprising a specific sulfonylurea compound, an ethoxylated fatty amine type surfactant and a vegetable oil and/or a mineral oil. However, further studies have been required to accomplish formulations which are sufficiently practical and which also have high added value.

Under these circumstances, the present inventors have conducted extensive studies to solve the above problems and as a result, have accomplished the present invention.

DISCLOSURE OF THE INVENTION

Namely, in order to cope with the above problems, the present inventors have conducted studies paying attention to herbicidal effects and toxicity and further paying attention to safety for human and environment. As a result, they have found a herbicidal suspension containing a sulfonylurea compound or its salt as an active ingredient, which is sufficiently practicable such as having favorable physical and chemical characteristics, and which has an advantage such as more excellent herbicidal activity or improved safety for crops.

The present invention provides a herbicidal suspension comprising (1) a sulfonylurea compound or its salt as a herbicidal component, (2) at least one surfactant selected from the group consisting of an alkoxylated sorbitol fatty acid ester and an alkoxylated sorbitan fatty acid ester, and (3) a water-immiscible diluent; and a method for controlling undesired plants or inhibiting their growth by means of such a herbicidal suspension.

BEST MODE FOR CARRYING OUT THE INVENTION

The sulfonylurea compound is a compound having the following partial structure:

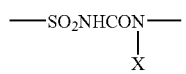

(wherein X is a hydrogen atom or an alkyl group), and it may, for example, be amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucetosulfuron, flupyrsulfuron, foramsulfuron, halosulfuron-methyl, imazosulfuron, iodosulfuron, isosulfuron-methyl, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl or tritosulfuron. Among them, azimsulfuron, bensulfuron-methyl, flazasulfuron or nicosulfuron is preferred.

As the salt of such a sulfonylurea compound, various types may be mentioned. It may, for example, be a salt with an alkali metal such as sodium or potassium, a salt with an alkaline earth metal such as magnesium or calcium, or a salt with an amine such as monomethylamine, dimethylamine or triethylamine.

The alkoxylated sorbitol fatty acid ester or the alkoxylated sorbitan fatty acid ester has one or more alkylene oxide moieties at optional positions. Such an alkylene oxide moiety may, for example, be ethylene oxide, propylene oxide, a copolymer thereof or a block copolymer thereof. Among them, ethylene oxide is preferred. The average addition molar amount of the alkylene oxide is from 3 to 150 mols, preferably from 3 to 60 mols.

The number of fatty acid ester in the alkoxylated sorbitol fatty acid ester or the alkoxylated sorbitan fatty acid ester may be one or more, and a monoester, a diester, a triester, a tetraester, a pentaester or a hexaester may, for example, be mentioned. Further, in a case where there are a plurality of fatty acid esters, they may be the same or different.

The fatty acid moiety of the alkoxylated sorbitol fatty acid ester or the alkoxylated sorbitan fatty acid ester may be either saturated or unsaturated and may be linear or branched, and its carbon number may be from about 4 to about 24, preferably from about 10 to about 20. The fatty acid may, for example, be a saturated fatty acid such as butyric acid, n-caproic acid, caprylic acid, n-capric acid, lauric acid, myristic acid, palmitic acid, stearic acid, isostearic acid or arachic acid, or an unsaturated fatty acid such as palmitoleic acid, oleic acid, linoleic acid, linolenic acid, monoctic acid, arachidonic acid or docosahexaenoic acid. Lauric acid, stearic acid or oleic acid is, for example, preferred.

The water-immiscible diluent may, for example, be a vegetable oil, a fatty acid derived from a vegetable oil, an alkyl ester of the fatty acid (including one having a fatty acid moiety in a vegetable oil alkylated, such as methylated vegetable oil or methylated seed oil) or a mineral oil.

The vegetable oil may, for example, be olive oil, is kapok oil, castor oil, papaya oil, camellia oil, coconut oil, sesame oil, corn oil, rice bran oil, peanut oil, cottonseed oil, soybean oil, rapeseed oil, linseed oil, tung oil, sunflower oil or safflower oil.

The fatty acid derived from a vegetable oil is a fatty acid derived from the above-described vegetable oil or the like and it may, for example, be a $C_{12-22}$ saturated or unsaturated fatty acid, such as lauric acid, palmitic acid, stearic acid, oleic acid, linolic acid, linoleic acid, erucic acid or brassidic acid, and the alkyl ester of the fatty acid may, for example, be a $C_{1-18}$ linear or branched alkyl ester, such as a methyl ester, a butyl ester, an isobutyl ester or an oleyl ester.

The mineral oil may, for example, be an aliphatic hydrocarbon such as liquid paraffin or paraffinic petroleum, or an aromatic hydrocarbon such as an alkyl benzene or an alkyl naphthalene.

The above water-immiscible diluents may be a mixture as the case requires.

The herbicidal suspension contains (1) a sulfonylurea compound or its salt as a herbicidal component, (2) at least one surfactant (hereinafter referred to as an essential surfactant) selected from the group consisting of an alkoxylated sorbitol fatty acid ester and an alkoxylated sorbitan fatty acid ester and (3) a water-immiscible diluent, and it is prepared as an oil-based herbicidal suspension such as an oil-based suspension concentrate or a gel formulation. For its preparation, various additives may be used as the case requires. Various additives which can be used here may be any additives so long as they are commonly used in this technical field, and for example, another surfactant (a surfactant other than the alkoxylated sorbitol fatty acid ester and the alkoxylated sorbitan fatty acid ester), a solvent, an anti-settling agent, a thickener, an anti-foaming agent, an antifreezing agent, an antioxidant, a gelling agent, a dispersion stabilizer, a phytotoxicity reducing agent, an anti-mold agent, a stabilizer, a preservative, and an inorganic ammonium salt, may be mentioned. The following may, for example, be mentioned as specific examples of such various additives. Further, such formulations may be prepared in accordance with methods commonly employed in this technical field.

The another surfactant includes, for example, anionic surfactants such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a polyoxyethylene styrylaryl ether sulfate, an ammonium polyoxyethylene styrylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a polyoxyethylene styrylaryl ether phosphoric acid ester or its salt, a salt of a condensate of naphthalene sulfonate with formalin, a salt of a condensate of alkylnaphthalene sulfonate with formalin, a salt of a condensate of phenol sulfonate with formalin and a salt of maleic anhydride alkylene copolymer; nonionic surfactants such as a sorbitan fatty acid ester, a glycerin fatty acid ester, a fatty acid polyglyceride, a fatty acid alcohol polyglycol ether, an acetylene glycol, an acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxyethylene castor oil, a polyoxypropylene fatty acid ester and an alkyl polyglycoside, and cationic surfactants such as an alkoxylated fatty amine. If desired, two or more of them may suitably be used in combination.

In the present invention, the herbicidal suspension preferably contains as another surfactant at least one surfactant selected from the group consisting of the above anionic surfactants, nonionic surfactants and cationic surfactants. Among them, the anionic surfactant is preferably an alkylaryl sulfonate, the nonionic surfactant is preferably a polyoxyethylene castor oil, and the cationic surfactant is preferably an alkoxylated fatty amine. The herbicidal suspension particularly preferably contains a combination thereof.

The full effect of the essential surfactant will be achieved when the cationic surfactant such as an alkoxylated fatty amine as the another surfactant is incorporated in the herbicidal suspension of the present invention. More particularly, the alkoxylated fatty amine may, for example, be ethoxylated tallow amine, ethoxylated soy amine or ethoxylated coco amine. The average addition molar amount of the alkylene oxide is from 3 to 100, preferably from 5 to 50. Such an embodiment is one of the preferred embodiments of the present invention.

The solvent may, for example, be water, solvent naphtha, paraffin, dioxane, acetone, isophorone, methyl isobutyl ketone, chlorobenzene, cyclohexane, dimethyl sulfoxide, dimethylformamide, N-methyl-2-pyrrolidone, an alcohol, acetic acid, butyric acid, isopropyl acetate, butyl acetate, benzene, an alkylbenzene or an alkylnaphthalene. If desired, two or more of them may suitably be used in combination.

The anti-settling agent may, for example, be silica, bentonite-alkylamino complex, bentonite, white carbon or aluminum magnesium silicic acid. If desired, two or more of them may be suitably used in combination.

The thickener may, for example, be a heteropolysaccharide such as xanthan gum or guar gum, a water-soluble polymer such as polyvinyl alcohol, a sodium salt of carboxymethyl cellulose or sodium alginate, bentonite or white carbon. If desired, two or more of them may suitably be used in combination.

The antifoaming agent may, for example, be polydimethylsiloxane or acetylene alcohol. If desired, two or more of them may suitably be used in combination.

The antifreezing agent may, for example, be ethylene glycol, propylene glycol, glycerin or urea. If desired, two or more of them may suitably be used in combination.

The gelling agent may, for example, be silica, organic attapulgite, clay, hydrogenated castor oil, a higher fatty acid ester, a higher alcohol, a salt of dialkyl sulfosuccinic acid ester, a benzoate, an alkyl sulfate, a poly acrylic polymer, or a mixture of a poly acrylic acid copolymer and water, or 12-hydroxystearic acid. If desired, two or more of them may suitably be used in combination.

The stabilizer may, for example, be urea.

The preservative may, for example, be formalin, p-chloro m-xylenol or 1,2-benzisothiazolin-3-one. If desired, two or more of them may suitably be used in combination.

In preparation of the herbicidal suspension of the present invention, the essential surfactant and optional another surfactant may be preliminarily combined, and then the other various components are mixed therewith. Specifically, a surfactant mixture comprising the essential surfactant and the optional another surfactant such as an anionic surfactant or a nonionic surfactant may be preliminarily prepared and used. In such a case, the surfactant mixture is prepared so that the amount of the essential surfactant is usually at least 40 parts by weight, preferably from 40 to 90 parts by weight. Such an embodiment is one of the preferred embodiments of the present invention.

In the present invention, if desired, another herbicidal compound other than the sulfonylurea compound or its salt may be used in combination, whereby more excellent effects and functionality may be achieved in some cases. For example, the range of plants to be killed may be broadened, the stage at which the herbicidal suspension is applied may be broadened, or the herbicidal activity may be improved in some cases. The sulfonylurea compound or its salt and the another herbicidal compound may be separately prepared and mixed at the time of application, or they may be prepared into one composition. The present invention includes the above combined herbicidal composition and a method of controlling undesired plants or inhibiting their growth by means of such a composition.

As the another herbicidal compound which can be used in combination with the sulfonylurea compound or its salt, the compound groups of the following (1) to (11) (common names, code names) may, for example, be mentioned. Even when not specifically mentioned, in a case where such compounds have salts, alkyl esters or various structural isomers such as optical isomers, they are, of course, all included.

(1) Those which are believed to exhibit herbicidal effects by disturbing hormone activities of plants, such as a phenoxy type such as 2,4-D, 2,4-DB, 2,4-DP, MCPA, MCPB, MCPP or naproanilide, an aromatic carboxylic acid type such as 2,3,6-TBA, dicamba, dichlobenil, picloram, triclopyr, clopyralid or aminopyralid, and others such as naptalam, benazolin, quinclorac, quinmerac, diflufenzopyr and thiazopyr.

(2) Those which are believed to exhibit herbicidal effects by inhibiting photosynthesis of plants, such as a urea type such as chlorotoluron, diuron, fluometuron, linuron, isoproturon, metobenzuron or tebuthiuron, a triazine type such as simazine, atrazine, atratone, simetryn, prometryn, dimethametryn, hexazinone, metribuzin, terbuthylazine, cyanazine, ametryn, cybutryne, triaziflam or propazine, a uracil type such as bromacil, lenacil or terbacil, an anilide type such as propanil or cypromid, a carbamate type such as swep, desmedipham or phenmedipham, a hydroxybenzonitrile type such as bromoxynil, bromoxynil-octanoate or ioxynil, and others such as pyridate, bentazone, amicarbazone and methazole.

(3) Quaternary ammonium salt type such as paraquat or diquat, which is believed to be converted to free radicals by itself to form active oxygen in the plant body.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen-sodium, fomesafen, oxyfluorfen, lactofen or ethoxyfen-ethyl, a cyclic imide type such as chlorphthalim, flumioxazin, flumiclorac-pentyl or fluthiacet-methyl, and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, metobenzuron, cinidon-ethyl, flupoxam, fluazolate, profluazol, pyrachlonil and flufenpyr-ethyl.

(5) Those which are believed to exhibit herbicidal effects characterized by whitening activities by inhibiting chromogenesis of plants such as carotenoids, such as a pyridazinone type such as norflurazon, chloridazon or metflurazon, a pyrazole type such as pyrazolate, pyrazoxyfen, benzofenap or BAS-670H, and others such as amitrol, fluridone, flurtamone, diflufenican, methoxyphenone, clomazone, sulcotrione, mesotrione, AVH-301, isoxaflutole, difenzoquat, isoxachlortole, benzobicyclon, picolinafen and beflubutamid.

(6) Those which exhibit strong herbicidal effects specifically to gramineous plants, such as an aryloxyphenoxypropionic acid type such as diclofop-methyl, flamprop-M-methyl, pyriphenop-sodium, fluazifop-butyl, haloxyfop-methyl, quizalofop-ethyl, cyhalofop-butyl, fenoxaprop-ethyl or metamifop-propyl, and a cyclohexanedione type such as alloxydim-sodium, clethodim, sethoxydim, tralkoxydim, butroxydim, tepraloxydim, caloxydim, clefoxydim or profoxydim.

(7) Those which are believed to exhibit herbicidal effects by inhibiting an amino acid biosynthesis of plants, such as a triazolopyrimidinesulfonamide type such as flumetsulam, metosulam, diclosulam, cloransulam-methyl, florasulam, metosulfam or penoxsulam, an imidazolinone type such as imazapyr, imazethapyr, imazaquin, imazamox, imazameth, imazamethabenz or is imazapic, a pyrimidinylsalicylic acid type such as pyrithiobac-sodium, bispyribac-sodium, pyriminobac-methyl, pyribenzoxim or pyriftalid, a sulfonylaminocarbonyltriazolinone type such as flucarbazone or procarbazone-sodium, and others such as glyphosate-ammonium, glyphosate-isopropylamine, glufosinate-ammonium and bialaphos.

(8) Those which are believed to exhibit herbicidal effects by inhibiting cell mitoses of plants, such as a dinitroaniline type such as trifluralin, oryzalin, nitralin, pendimethalin, ethalfluralin, benfluralin or prodiamine, an amide type such as bensulide, napronamide or pronamide an organic phosphorus type such as amiprofos-methyl, butamifos, anilofos or piperophos, a phenylcarbamate type such as propham, chlorpropham or barban, a cumylamine type such as daimuron, cumyluron or bromobutide, and others such as asulam, dithiopyr and thiazopyr.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachloror propisochlor, a carbamate type such as molinate, dimepiperate or pyributicarb, and others such as etobenzanid, mefenacet, flufenacet, tridiphane, cafenstrole, fentrazamide, oxaziclomefone, indanofan, dimethenamid and benfuresate.

(10) A thiocarbamate type such as EPTC, butylate, vernolate, pebulate, cycloate, prosulfocarb, esprocarb, thiobencarb, diallate or triallate, and others such as MSMA, DSMA, endothall, ethofumesate, sodium chlorate, pelargonic acid, fosamine, pinoxaden and HOK-201.

(11) Those which are believed to exhibit herbicidal effects by being parasitic on plants, such as *Xanthomonas campestris, Epicoccosurus nematosurus, Exserohilum monoseras* and *Drechsrela monoceras*.

In the present invention, blend proportions of various components cannot generally be defined, since they may suitably be changed depending upon the types of the blend components, the formulations or the application sites. A formulation may, for example, be prepared by incorporating the sulfonylurea compound or its salt in a proportion of from 0.5 to 20 parts by weight, preferably from 2 to 10 parts by weight, furthermore preferably from 5 to 10 parts by weight; the essential surfactant in a proportion of from 0.5 to 35 parts by weight, preferably from 1 to 25 parts by weight; another surfactant, if incorporated as the case requires, in a proportion of from 0.5 to 55 parts by weight, preferably from 1 to 40 parts by weight; a solvent, if incorporated as the case requires, in a proportion of from 0.1 to 30 parts by weight, preferably from 0.5 to 20 parts by weight, an anti-settling agent, if incorporated as the case requires, in a proportion of from 0.1 to 10 parts by weight, preferably from 0.5 to 5 parts by weight; a gelling agent, if incorporated as the case requires, in a proportion of from 0.1 to 50 parts by weight, preferably from 5 to 40 parts by weight; a stabilizer, if incorporated as the case requires, in a proportion of from 0.1 to 20 parts by weight, preferably from 1 to 10 parts by weight; another herbicidal compound, if incorporated as the case requires, in a proportion of from 0.5 to 75 parts by weight, preferably from 0.5 to 50 parts by weight, and the water-immiscible diluent as the rest, so that the total would be 100 parts by weight.

The herbicidal suspension of the present invention thus prepared has favorable and selective herbicidal effect since when it is diluted with water at the time of its use, droplets of oil will be well dispersed, whereby excellent emulsion characteristics will be achieved.

The herbicidal suspension of the present invention is capable of controlling a wide range of weeds including, for example, sedges (or Cyperaceae) such as rice flatsedge (*Cyperus iria* L.) or purple nutsedge (*Cyperus rotundus* L.), grasses (or gramineae) such as barnyardgrass (*Echinochloa crus-galli* L.), crabgrass (*Digitaria sanguinalis* L.), green foxtail (*Setaria viridis* L.), goosegrass (*Eleusine indica* L.), wild oat (*Avena fatua* L.), johnsongrass (*Sorghum halepense* L.) or quackgrass (*Agropyron repens* L.), and broadleaves such as velvetleaf (*Abutilon theophrasti* MEDIC.), tall morning glory (*Ipomoea purpurea* L.), common lambsquarters (*Chenopodium album* L.), prickly sida (*Sida spinosa* L.), common purslane (*Portulaca oleracea* L.), redroot pigweed (*Amaranthus retroflexus* L.), sicklepod (*Cassia obtusifolia* L.), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) or threeseeded copperleaf (*Acalypha australis* L.), or inhibiting their growth, by applying it to such undesired plants or to a place where they grow, for example, by foliar application. Accordingly, its application range extends not only to crop plant fields but also agricultural fields such as orchards, mulberry fields or paddy fields and non-agricultural fields such as forest land, farm roads, play grounds, factory sites or grass plots. The sulfonylurea compound or its salt may be applied in an amount of 1 to 500 g/ha, preferably from 2 to 250 g/ha. Particularly, a herbicidal suspension comprising nicosulfuron or its salt is capable of controlling noxious weeds or inhibiting their growth without presenting phytotoxicity to corn, and it is very useful as a herbicidal composition for corn fields. Nicosulfuron may be applied in an amount of from 2 to 400 g/ha, preferably from 5 to 200 g/ha.

EXAMPLES

Now, the present invention will be described in further detail with reference to Examples. However, it should be understood that the present invention is by no means restricted to such specific Examples.

Example 1

(1) Nicosulfuron (purity: 94.5%): 7.23 parts by weight
(2) Mixture (surfactant A) containing polyoxyethylene sorbitol tetraoleate as the main component and containing polyoxyethylene castor oil and calcium salt of dodecylbenzenesulfonic acid: 10.35 parts by weight
(3) Ethoxylated tallow amine (surfactant B): 15.53 parts by weight
(4) Bentonite-alkylamino complex: 1.03 parts by weight
(5) Urea: 3.11 parts by weight
(6) Mixture of methylated seed oil and corn oil: 62.75 parts by weight
The above components were mixed, and the mixture was wet-milled by a wet-mill for 15 minutes to prepare an oil-based suspension concentrate.

Example 2

(1) Nicosulfuron (purity: 94.5%): 7.23 parts by weight
(2) Surfactant A: 10.35 parts by weight
(3) Surfactant B: 15.53 parts by weight
(4) Bentonite-alkylamino complex: 1.03 parts by weight
(5) Urea: 3.11 parts by weight
(6) Mixture of methylated seed oil and corn oil: 60.68 parts by weight
(7) Alcohol: 2.07 parts by weight The above components were mixed, and the mixture was wet-milled by a wet-mill for 15 minutes to prepare an oil-based suspension concentrate.

Example 3

(1) Nicosulfuron (purity: 94.5%): 7.23 parts by weight
(2) Surfactant A: 10.35 parts by weight
(3) Surfactant B: 15.53 parts by weight
(4) Bentonite-alkylamino complex: 1.03 parts by weight
(5) Urea: 3.11 parts by weight
(6) Mixture of methylated seed oil and corn oil: 55.25 parts by weight
(7) Alcohol: 7.50 parts by weight
The above components were mixed, and the mixture was wet-milled by a wet-mill for 15 minutes to prepare an oil-based suspension concentrate.

Example 4

(1) Nicosulfuron (purity: 94.5%): 7.23 parts by weight
(2) Mixture (surfactant D) containing polyoxyethylene sorbitan trioleate as the main component and containing polyoxyethylene castor oil and calcium salt of dodecylbenzenesulfonic acid: 10.35 parts by weight
(3) Surfactant B: 20.70 parts by weight
(4) Hydrophobic fumed silica: 1.03 parts by weight
(5) Urea: 1.03 parts by weight
(6) Corn oil: 54.48 parts by weight
(7) Alcohol: 5.18 parts by weight
The above components were mixed, and the mixture was wet-milled by a wet-mill for 15 minutes to prepare an oil-based suspension concentrate.

Example 5

(1) Flazasulfuron (purity: 95.1%): 7.14 parts by weight
(2) Surfactant A: 10.35 parts by weight
(3) Surfactant B: 20.70 parts by weight
(4) Hydrophobic fumed silica: 1.04 parts by weight
(5) Urea: 3.11 parts by weight
(6) Corn oil: 52.48 parts by weight
(7) Alcohol: 5.18 parts by weight
The above components were mixed, and the mixture was wet-milled by a wet-mill for 15 minutes to prepare an oil-based suspension concentrate.

Example 6

(1) Azimsulfuron (purity: 99.0%): 7.14 parts by weight
(2) Surfactant A: 10.35 parts by weight
(3) Surfactant B: 20.70 parts by weight
(4) Hydrophobic fumed silica: 1.04 parts by weight
(5) Urea: 3.11 parts by weight
(6) Corn oil: 52.48 parts by weight
(7) Alcohol: 5.18 parts by weight
The above components were mixed, and the mixture was wet-milled by a wet-mill for 15 minutes to prepare an oil-based suspension concentrate.

Example 7

(1) Bensulfuron-methyl (purity: 99.3%): 7.14 parts by weight
(2) Surfactant A: 10.35 parts by weight
(3) Surfactant B: 20.70 parts by weight
(4) Hydrophobic fumed silica: 1.04 parts by weight (5) Urea: 3.11 parts by weight
(6) Corn oil: 52.48 parts by weight
(7) Alcohol: 5.18 parts by weight The above components were mixed, and the mixture was wet-milled by a wet-mill for 15 minutes to prepare an oil-based suspension concentrate.

Comparative Example 1

An oil-based suspension concentrate was prepared in the same manner as in Example 1 except that a mixture (surfactant C) of polyoxyethylene hydrogenated castor oil and dioctylsulfosuccinate was used instead of the surfactant A.

Comparative Example 2

An oil-based suspension concentrate was prepared in the same manner as in Example 2 except that the surfactant C was used instead of the surfactant A.

Comparative Example 3

An oil-based suspension concentrate was prepared in the same manner as in Example 3 except that the surfactant C was used instead of the surfactant A.

Comparative Example 4

An oil-based suspension concentrate was prepared in the same manner as in Example 4 except that the surfactant C was used instead of the surfactant D.

Comparative Example 5

An oil-based suspension concentrate was prepared in the same manner as in Example 5 except that the surfactant C was used instead of the surfactant A.

Comparative Example 6

An oil-based suspension concentrate was prepared in the same manner as in Example 6 except that the surfactant C was used instead of the surfactant A.

Comparative Example 7

An oil-based suspension concentrate was prepared in the same manner as in Example 7 except that the surfactant C was used instead of the surfactant A.

Comparative Example 8

An oil-based suspension concentrate was prepared in the same manner as in Example 1 except that a mixture (surfactant E) of polyoxyethylene nonylphenyl ether, dialkylsulfosuccinate, polyoxyethylene hydrogenated castor oil and polyglycerol esters of fatty acid was used instead of the surfactant A.

Comparative Example 9

An oil-based suspension concentrate was prepared in the same manner as in Example 2 except that the surfactant E was used instead of the surfactant A.

Comparative Example 10

An oil-based suspension concentrate was prepared in the same manner as in Example 3 except that the surfactant E was used instead of the surfactant A.

Now, Test Examples of the present invention will be described below.

Test Example 1

Each of the oil-based suspension concentrates obtained in Examples and Comparative Examples was diluted with ion-exchange water and charged into a circulation bath of a particle size measuring apparatus (MICROTRAC HRA, model 9320-x100, HONEYELL), followed by circulation for 5 minutes. The droplets size of emulsion diluted 1,500 to 2,000 times was measured. The results are shown in Table 1.

TABLE 1

|  | Oil-based suspension concentrate | Droplets size of emulsion (μm) (average) |
| --- | --- | --- |
| Present invention | Example 1 | 18.0 |
|  | Example 2 | 15.9 |
|  | Example 3 | 13.3 |
| Comparison | Comparative Example 1 | 21.4 |
|  | Comparative Example 2 | 22.0 |
|  | Comparative Example 3 | 15.8 |

The conditions in this test correspond to a state where the herbicidal suspension is diluted with water at the time of application.

The oil-based suspension concentrates prepared in Comparative Examples 1 to 3 corresponding to formulations similar to formulations as disclosed in Examples of EP 0598515, the oil-based suspension concentrates were under a certain emulsified condition, whereas the oil-based suspension concentrates which were herbicidal suspensions of the present invention prepared in Examples 1 to 3 were under a more finely emulsified condition, such being excellent.

Test Example 2

Each of the oil-based suspension concentrates obtained in Examples and Comparative Examples was diluted with CIPAC Standard Water D 600 times, and the diluted concentrate was left at rest for 15 minutes. The diluted concentrate was put in a measurement cell, and measurement was carried out by a calorimeter (CT-310, manufactured by MINOLTA CAMERA Co.) by means of L*a*b* color system (JIS Z 8729: 2004) to determine the color difference (ΔE) between Example and the corresponding Comparative Example from the following formula. The is results are shown in Table 2.

$$\Delta E = (\Delta L^2 + \Delta a^2 + \Delta b^2)^{1/2}$$

TABLE 2

| Oil-based suspension concentrate | Luminosity (L*) | Chromaticity (a*) | Chromaticity (b*) | Color difference (ΔE) |
| --- | --- | --- | --- | --- |
| Example 1 | 57.05 | 0.54 | 6.62 | 13.45 |
| Comparative Example 1 | 70.42 | 0.42 | 5.15 |  |
| Example 2 | 58.48 | 0.14 | 4.49 | 7.25 |
| Comparative Example 2 | 65.63 | 0.43 | 5.63 |  |
| Example 3 | 52.44 | 0.88 | 8.08 | 8.58 |
| Comparative Example 3 | 60.92 | 1.28 | 9.32 |  |

The luminosity (L*) is represented by a numerical value of from 0 to 100, and the larger the value, the brighter (the luminosity of the ion-exchanged water is about 100). As shown in Table 2, the luminosities of the oil-based suspension concentrates which are herbicidal suspensions of the present invention in Examples 1 to 3 are smaller than those of the corresponding Comparative Examples 1 to 3. Accordingly, it is understood that the oil-based suspension concentrates of Examples 1 to 3 have deeper color (emulsified condition).

Further, the color difference (ΔE) is evaluated based on evaluation standards (NBS unit, National Bureau of Standard) as shown in the following Table 3 and as a result, there is a significant difference between the herbicidal suspensions of the present invention prepared in Examples 1 to 3 and the concentrates prepared in the corresponding Comparative Examples 1 to 3.

TABLE 3

| Color difference (ΔE) | Sensual difference |
| --- | --- |
| 0 to 0.5 | Trace |
| 0.5 to 1.5 | Slight |
| 1.5 to 3.0 | Noticeable |
| 3.0 to 6.0 | Appreciable |
| 6.0 to 12.0 | Much |
| More than 12.0 | Very much |

Test Example 3

Upland field soil was filled in a 1/1,000,000 ha pot, seeds of crabgrass (*Digitaria sanguinalis* L.) were sown therein and grown in a green house. When crabgrass reached 3 leaf stage, a prescribed amount (17.5 g a.i./ha) of each of the oil-based suspension concentrates prepared in Examples and Comparative Examples, was diluted with water corresponding to 300 liters/ha, followed by foliar application.

On the 21st day after the application of the herbicide, the growth of crabgrass was visually observed (growth inhibition rate (%)=0:untreated plot to 100:complete kill), whereby the results as shown in Table 4 were obtained.

TABLE 4

| | Oil-based suspension concentrate | Growth inhibition rate (%) |
| --- | --- | --- |
| Present invention | Example 1 | 70 |
| | Example 2 | 76 |
| Comparison | Comparative Example 1 | 58 |
| | Comparative Example 2 | 63 |

Test Example 4

Upland field soil was filled in a 1/1,000,000 ha pot, seeds of corn (*Zea mays*) were sown therein and grown in a green house in winter. When corn reached 3 leaf stage, a prescribed amount (90 g a.i./ha) of each of the oil-based suspension concentrates prepared in Examples and Comparative Examples was diluted with water corresponding to 300 liters/ha, followed by foliar application.

On the 14th day after the application of the herbicide, the growth of corn was visually observed and as a result, the oil-based suspension concentrates which were herbicidal suspensions of the present invention prepared in Examples 1 to 3 exhibited a low degree of corn growth inhibition and showed more excellent safety for the crops as compared with the corresponding Comparative Examples 1 to 3.

Test Example 5

With respect to the oil-based suspension concentrates prepared in the above Example and Comparative Example, the droplets size of emulsion was measured in accordance with the above Test Example 1. The results are shown in Table 5.

TABLE 5

| | Oil-based suspension concentrate | Droplets size of emulsion (μm) (average) |
| --- | --- | --- |
| Present invention | Example 4 | 17.4 |
| Comparison | Comparative Example 4 | 23.1 |

The oil-based suspension concentrate prepared in Comparative Example 4 corresponding to a formulation similar to the formulation as disclosed in Example of EP 0598515 was under a certain emulsified condition, whereas the oil-based suspension concentrate which was a herbicidal suspension of the present invention prepared in Example 4 was under a more finely emulsified condition, such being excellent.

Test Example 6

With respect to the oil-based suspension concentrates prepared in the above Examples and Comparative Examples, the droplets size of emulsion was measured in accordance with the above Test Example 1. The results are shown in Table 6.

TABLE 6

| | Oil-based suspension concentrate | Droplets size of emulsion (μm) (average) |
| --- | --- | --- |
| Present invention | Example 5 | 17.2 |
| | Example 6 | 14.7 |
| | Example 7 | 13.6 |
| Comparison | Comparative Example 5 | 22.6 |
| | Comparative Example 6 | 22.6 |
| | Comparative Example 7 | 29.8 |

The oil-based suspension concentrates prepared in Comparative Examples 5 to 7 were under a certain emulsified condition, whereas the oil-based suspension concentrates which were herbicidal suspensions of the present invention prepared in Examples 5 to 7 were under a more finely emulsified condition, such being excellent.

Test Example 7

With respect to the oil-based suspension concentrates prepared in the above Examples and Comparative Examples, the droplets size of emulsion was measured in accordance with the above Test Example 1. The results are shown in Table 7.

TABLE 7

| | Oil-based suspension concentrate | Droplets size of emulsion (μm) (average) |
| --- | --- | --- |
| Present invention | Example 1 | 17.3 |
| | Example 2 | 15.9 |
| | Example 3 | 13.5 |

TABLE 7-continued

|  | Oil-based suspension concentrate | Droplets size of emulsion (μm) (average) |
|---|---|---|
| Comparison | Comparative Example 8 | 22.2 |
|  | Comparative Example 9 | 19.7 |
|  | Comparative Example 10 | 17.4 |

The oil-based suspension concentrates prepared in Comparative Examples 8 to 10 corresponding to preparations as disclosed in Examples of EP 0598515 were under a certain emulsified condition, whereas the oil-based suspension concentrates which were herbicidal suspensions of the present invention prepared in Examples 1 to 3 were under a more finely emulsified condition, such being excellent.

Test Example 8

With respect to the oil-based suspension concentrates prepared in the above Example and Comparative Example, the luminosity and the chromaticities were measured to determine the color difference in accordance with the above Test Example 2. The results are shown in Table 8.

TABLE 8

| Oil-based suspension concentrate | Luminosity (L*) | Chromaticity (a*) | Chromaticity (b*) | Color difference (ΔE) |
|---|---|---|---|---|
| Example 4 | 49.38 | −0.15 | 6.39 | 4.51 |
| Comparative Example 4 | 53.83 | 0.07 | 7.09 |  |

Since the luminosity (L*) of the oil-based suspension concentrate which is a herbicidal suspension of the present invention prepared in Example 4 is small as compared with the corresponding Comparative Example 4, it is understood that the oil-based suspension concentrate in Example 4 has a deeper color (emulsified condition).

Further, it is also understood that there is a significant difference between them with regard to the color difference (ΔE).

Test Example 9

With respect to the oil-based suspension concentrates prepared in the above Examples and Comparative Examples, the luminosity and the chromaticities were measured to determine the color difference in accordance with the above Test Example 2. The results are shown in Table 9.

TABLE 9

| Oil-based suspension concentrate | Luminosity (L*) | Chromaticity (a*) | Chromaticity (b*) | Color difference (ΔE) |
|---|---|---|---|---|
| Example 5 | 34.80 | −0.25 | 3.80 | 17.4 |
| Comparative Example 5 | 52.19 | −0.53 | 3.68 |  |
| Example 6 | 33.05 | −0.26 | 3.80 | 17.5 |
| Comparative Example 6 | 50.52 | −0.54 | 3.11 |  |
| Example 7 | 44.29 | −0.43 | 5.03 | 10.5 |
| Comparative Example 7 | 54.74 | −0.58 | 4.41 |  |

Since the luminosities (L*) of the oil-based suspension concentrates which are herbicidal suspensions of the present invention prepared in Example 5 to 7 are small as compared with the corresponding Comparative Examples 5 to 7, it is understood that the oil-based suspension concentrates in Example 5 to 7 have a deeper color (emulsified condition).

Further, it is also understood that there is a significant difference between Example and the corresponding Comparative Example, with regard to the color difference (ΔE).

Test Example 10

With respect to the oil-based suspension concentrates prepared in the above Examples and Comparative Examples, the luminosity and the chromaticities were measured to determine the color difference in accordance with the above Test Example 2. The results are shown in Table 10.

TABLE 10

| Oil-based suspension concentrate | Luminosity (L*) | Chromaticity (a*) | Chromaticity (b*) | Color difference (ΔE) |
|---|---|---|---|---|
| Example 1 | 48.57 | −0.35 | 4.81 | 9.96 |
| Comparative Example 8 | 58.41 | −0.34 | 6.34 |  |
| Example 2 | 44.75 | 0.15 | 6.53 | 11.04 |
| Comparative Example 9 | 55.79 | −0.07 | 6.34 |  |
| Example 3 | 48.13 | −0.05 | 6.17 | 10.6 |
| Comparative Example 10 | 58.28 | 0.14 | 7.68 |  |

Since the luminosities (L*) of the oil-based suspension concentrates which are herbicidal suspensions of the present invention prepared in Example 1 to 3 are small as compared with the corresponding Comparative Examples 8 to 10, it is understood that the oil-based suspension concentrates in Example 1 to 3 have a deeper color (emulsified condition).

Further, it is also understood that there is a significant difference between Example and the corresponding Comparative Example, with regard to the color difference (ΔE).

What is claimed is:

1. A herbicidal suspension comprising (1) a sulfonylurea compound which is at least one sulfonylurea compound selected from the group consisting of flazasulfuron and nicosulfuron, or its salt as a herbicidal component, (2) an alkoxylated sorbitol fatty acid ester, and (3) a water-immiscible diluent,
wherein component (2) is a polyoxyethylene sorbitol tetraoleate.

2. The herbicidal suspension according to claim 1, which comprises (1) from 0.5 to 20 parts by weight of the sulfonylurea compound or its salt, (2) from 0.5 to 35 parts by weight of the alkoxylated sorbitol fatty acid ester, and (3) the water-immiscible diluent as the main component of the rest.

3. The herbicidal suspension according to claim 1, wherein the water-immiscible diluent is at least one member selected from the group consisting of a vegetable oil, a fatty acid derived from a vegetable oil, an alkyl ester of the fatty acid and a mineral oil.

4. The herbicidal suspension according to claim 1, which further comprises another surfactant.

5. The herbicidal suspension according to claim 2, which further comprises from 0.5 to 55 parts by weight of another surfactant.

6. The herbicidal suspension according to claim 4, wherein the another surfactant is at least one surfactant selected from the group consisting of an anionic surfactant, a nonionic surfactant and a cationic surfactant.

7. The herbicidal suspension according to claim 4, wherein the another surfactant is an anionic surfactant.

8. The herbicidal suspension according to claim 7, wherein the anionic surfactant is an alkylaryl sulfonate.

9. The herbicidal suspension according to claim 4, wherein the another surfactant is a nonionic surfactant.

10. The herbicidal suspension according to claim 9, wherein the nonionic surfactant is at least one surfactant selected from the group consisting of polyoxyethylene castor oil and polyoxyethylene hydrogenated castor oil.

11. The herbicidal suspension according to claim 4, wherein the another surfactant is a cationic surfactant.

12. The herbicidal suspension according to claim 11, wherein the cationic surfactant is an alkoxylated fatty amine.

13. The herbicidal suspension according to claim 4, which further comprises as the another surfactant an alkylaryl sulfonate and an alkoxylated fatty amine.

14. The herbicidal suspension according to claim 4, which further comprises as the another surfactant an alkylaryl sulfonate, polyoxyethylene castor oil and an alkoxylated fatty amine.

15. A method for controlling undesired plants or inhibiting their growth, which comprises applying a herbicidally effective amount of the herbicidal suspension as defined in claim 1 to the undesired plants or to a place where they grow.

16. The herbicidal suspension according to claim 14, wherein the another surfactant comprises calcium dodecylbenzene sulfonate, polyoxyethylene castor oil and ethoxylated tallow amine.

* * * * *